(12) United States Patent
Hansen et al.

(10) Patent No.: US 10,314,536 B2
(45) Date of Patent: Jun. 11, 2019

(54) METHOD AND SYSTEM FOR DELIVERING BIOMECHANICAL FEEDBACK TO HUMAN AND OBJECT MOTION

(71) Applicants: Ben Hansen, Bradenton, FL (US); Joe Nolan, Massapequa, NY (US); Keith Robinson, Seaford, NY (US); Dave Fortenbaugh, Birmingham, AL (US)

(72) Inventors: Ben Hansen, Bradenton, FL (US); Joe Nolan, Massapequa, NY (US); Keith Robinson, Seaford, NY (US); Dave Fortenbaugh, Birmingham, AL (US)

(73) Assignee: Core Sports Technology Group, LLC, Melville, NY (US)

( * ) Notice: Subject to any disclaimer, the term of this patent is extended or adjusted under 35 U.S.C. 154(b) by 0 days.

(21) Appl. No.: 15/794,579

(22) Filed: Oct. 26, 2017

(65) Prior Publication Data
US 2018/0177450 A1    Jun. 28, 2018

Related U.S. Application Data

(63) Continuation of application No. 14/660,338, filed on Mar. 17, 2015.
(Continued)

(51) Int. Cl.
*G06K 9/00* (2006.01)
*A61B 5/00* (2006.01)
(Continued)

(52) U.S. Cl.
CPC .............. *A61B 5/486* (2013.01); *A41D 1/002* (2013.01); *A41D 19/0027* (2013.01);
(Continued)

(58) Field of Classification Search
USPC .......................................... 382/103, 128–134
See application file for complete search history.

(56) References Cited

U.S. PATENT DOCUMENTS

2002/0177770 A1   11/2002   Lang
2005/0105772 A1    5/2005   Voronka
(Continued)

OTHER PUBLICATIONS

Marcus G. Pandy: "Computer Modeling and 1-15 Simulation of Human Movement", Annual Review of Biomedical Engineering, vol. 3, No. 1, Aug. 1, 2001 (Aug. 1, 2001), pp. 245-273, XP055413594.
(Continued)

*Primary Examiner* — Alex Kok S Liew
(74) *Attorney, Agent, or Firm* — Burns & Levinson LLP; Bruce D. Jobse

(57) ABSTRACT

A method and system to deliver biomechanical feedback utilizes three major elements: (1) multiple hardware data capture devices, including optical motion capture, inertial measurement units, infrared scanning devices, and two-dimensional RGB consecutive image capture devices, (2) a cross-platform compatible physics engine compatible with optical motion capture, inertial measurement units, infrared scanning devices, and two-dimensional RGB consecutive image capture devices, and (3) interactive platforms and user-interfaces to deliver real-time feedback to motions of human subjects and any objects in their possession and proximity.

17 Claims, 17 Drawing Sheets

Related U.S. Application Data

(60) Provisional application No. 61/954,375, filed on Mar. 17, 2014.

(51) Int. Cl.

| | | |
|---|---|---|
| *A61B 5/11* | (2006.01) | |
| *G16H 40/63* | (2018.01) | |
| *G06F 19/00* | (2018.01) | |
| *G09B 19/00* | (2006.01) | |
| *A63B 60/46* | (2015.01) | |
| *A41D 1/00* | (2018.01) | |
| *A41D 19/00* | (2006.01) | |
| *A63B 24/00* | (2006.01) | |
| *A63B 71/06* | (2006.01) | |
| *A63B 59/50* | (2015.01) | |
| *A63B 49/00* | (2015.01) | |

(52) U.S. Cl.
CPC .......... *A61B 5/0075* (2013.01); *A61B 5/1121* (2013.01); *A61B 5/1128* (2013.01); *A61B 5/7475* (2013.01); *A63B 24/0003* (2013.01); *A63B 24/0021* (2013.01); *A63B 60/46* (2015.10); *A63B 71/0622* (2013.01); *G06F 19/3481* (2013.01); *G06K 9/00348* (2013.01); *G09B 19/0038* (2013.01); *G16H 40/63* (2018.01); *A41D 2600/10* (2013.01); *A61B 2576/00* (2013.01); *A63B 49/00* (2013.01); *A63B 59/50* (2015.10); *A63B 2220/12* (2013.01); *A63B 2220/803* (2013.01); *A63B 2220/806* (2013.01); *A63B 2220/807* (2013.01); *A63B 2220/833* (2013.01); *A63B 2220/836* (2013.01); *A63B 2225/50* (2013.01); *A63B 2230/04* (2013.01); *A63B 2230/40* (2013.01); *A63B 2230/60* (2013.01); *A63B 2230/65* (2013.01)

(56) References Cited

U.S. PATENT DOCUMENTS

| | | |
|---|---|---|
| 2005/0209536 A1 | 9/2005 | Dariush |
| 2008/0285805 A1 | 11/2008 | Luinge et al. |
| 2009/0024061 A1* | 1/2009 | Ueda .................. A61H 1/02 600/595 |
| 2010/0121227 A1 | 5/2010 | Stirling et al. |
| 2012/0259650 A1 | 10/2012 | Mallon et al. |
| 2013/0038745 A1 | 2/2013 | Myokan |
| 2013/0244211 A1 | 9/2013 | Dowling et al. |

OTHER PUBLICATIONS

International Search report in corresponding International Application No. PCT/US15/21004 dated May 24, 2015.

* cited by examiner

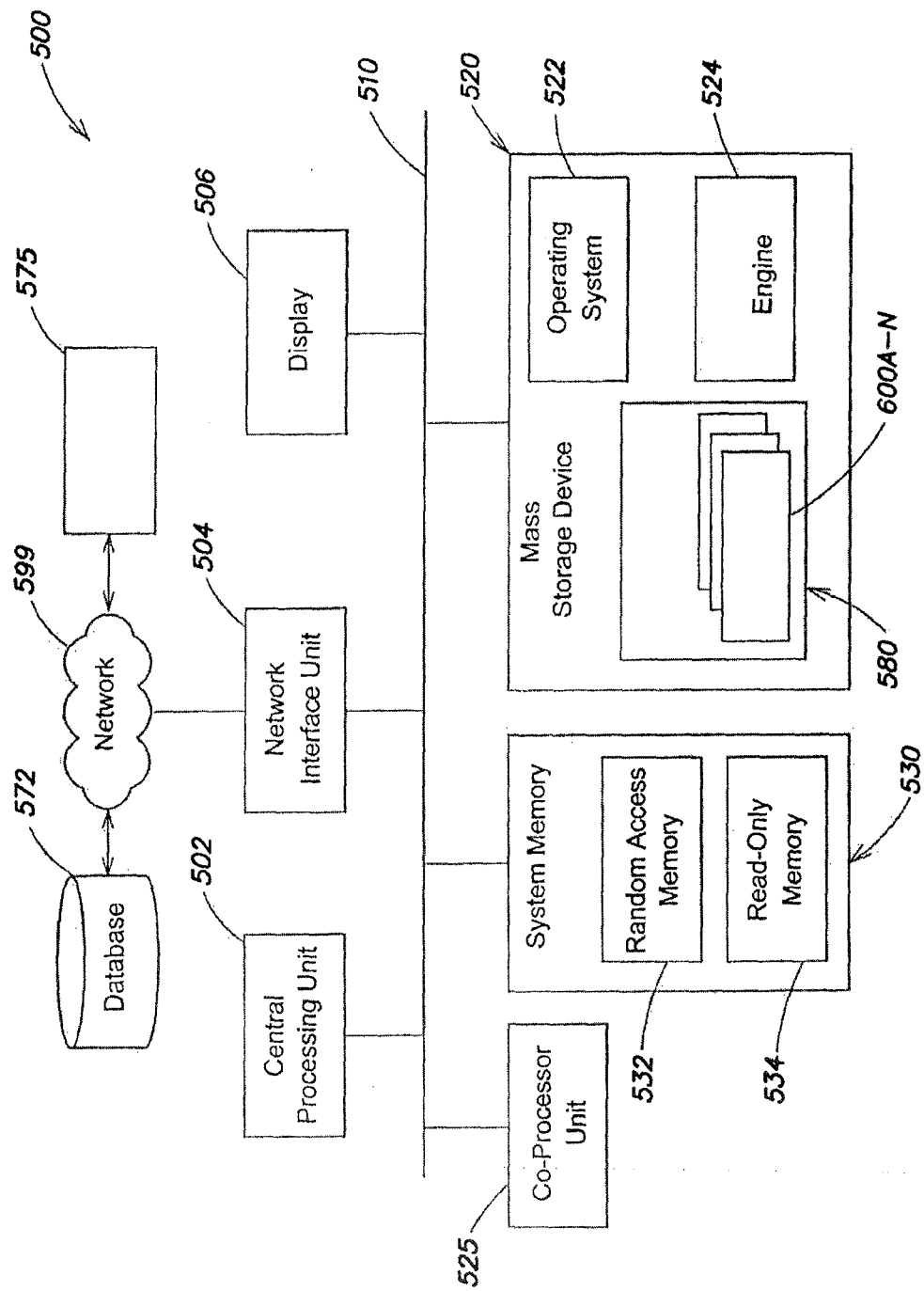

METHOD AND SYSTEM FOR DELIVERING BIOMECHANICAL FEEDBACK TO HUMAN AND OBJECT MOTION

FIELD OF THE INVENTION

This disclosure relates to a method and system for delivering biomechanical feedback to human and object motions.

BACKGROUND OF INVENTION

Systems capable of delivering human and object motion currently exist but are typically very sophisticated and expensive. As well, the format of the feedback provided by these systems varies considerably. Typically, there are no exhaustive methods and systems to deliver biomechanical feedback across multiple platforms and entities consistently. For example, optical motion capture is currently used in motion capture studios and sports technology companies to analyze humans and objects. These motion capture laboratories and studios focus on biomechanical research of human subjects to analyze performance, recovery, and injury risk identifiers, amongst others. Many biomechanical researchers develop proprietary software and processing algorithms to extract kinematic and kinetic measures of human and object motion. The application of physics engines to extract these metrics are based on the precision and location of retro-reflective markers on bony anatomical landmarks of the body and objects. Feedback is usually given in highly technical formats that often leave the test-subject unaware of the true underlying biomechanical flaw and fail to address corrective exercises, drills, and training regimens to improve performance and recovery, and reduce the risk of injury. As well, when and if prescriptive feedback is given, there are few methods to assess compliance with such feedback and there are few systems available for appropriate re-evaluation of the human subject and object.

Accordingly, a need exists for a system that provides biomechanical feedback in a format which is usable by an actor/athlete to improve their performance and reduce their risk of injury and that is supported by statistical relationship models, interactive platforms, and more advanced hardware platforms.

Wearable technology is becoming a primary means of assessing human and object motion. This technology is based upon embedding sensor technology in wearable garments. An example of such use is the ability to extract data from one or more on miniaturized accelerometers and gyroscopes for the purpose of reconstructing three-dimensional motion, however, there are limitations to the precision and accuracy of wearable technology that often misleads users with information that is not supported by statistical models. Wearable technology also does not provide comprehensive motion detection of all body and object segments, and, thus, does not allow for extensive prescriptive feedback to improve performance and recovery, and, thereby, reduce the risk of injury. Wearable technology is often wirelessly interfaced with mobile devices to compute kinematics and kinetics, and to display biomechanical feedback in single sessions. That said, there is no cross-platform continuity to keep users engaged, and few methods to monitor compliance and deliver significant feedback.

Accordingly, a further need exists for a system that incorporates advanced physics engine capabilities, advanced hardware processing and sensor technology, and interactive interfaces to produce meaningful data usable by an actor/athlete to improve their performance and reduce their risk of injury.

SUMMARY OF THE INVENTION

Disclosed is a method and system to deliver biomechanical feedback to subjects. The system utilizes three major elements: (1) multiple hardware data capture devices, including optical motion capture, inertial measurement units, infrared scanning devices, and two-dimensional RGB consecutive image capture devices, (2) a cross-platform compatible physics engine compatible with optical motion capture, inertial measurement units, infrared scanning devices, and two-dimensional RGB consecutive image capture devices, and (3) interactive platforms and user-interfaces to deliver real-time feedback to motions of humans and any objects in their possession and proximity.

The first element, a cross-platform compatible physics engine, imports data captured from a variety of hardware devices. Data imported from the hardware devices are then fed through kinematics and kinetics algorithms to extract desired biomechanical data. Data is then compiled by the physics engine across multiple subjects and across multiple sessions of a single subject. The physics engine also computes mechanical equivalencies to allow compatibility across hardware platforms. Mechanical equivalencies include correlating database data to injury and performance statistics, correlating discrete kinematics and kinetics of a body to discrete kinematics and kinetics of objects, principal component analysis to correlate time-series data of the body to objects, comparison of subject and object data to compiled databases, and extraction of prescriptive feedback based on all mechanical equivalencies The second element, the hardware data capture devices, may comprise a variety of peripheral devices that collect two-dimensional or three-dimensional motion data of subject or object. In one embodiment, such peripheral devices may comprise (1) optical motion capture devices to collect three-dimensional positional data on reflective markers placed on the body and/or an object, (2) inertial measurement units with gyroscopes and accelerometers placed on the body, on an object, or in garments, to collect three-dimensional translation and rotation motion data of object(s) or segment(s) of the subjects body, (3) infrared scanning devices, such as the Microsoft Kinect or Google Tango, to capture three-dimensional point clouds of movement data and incorporate skeletal and object tracking algorithms to extract three-dimensional joint and object positions, and (4) Red Green Blue (RGB) two-dimensional consecutive image capture devices to collect movement images and to incorporate skeletal and object tracking algorithms to extract three-dimensional joint and object positions and kinematics.

The hardware data capture devices of the second element may further comprise wearable sensor technology which utilizes motion sensing hardware embedded in wearable garments to compute human and object motion. The wearable technology may be coupled the physics engine and interactive interface to offer prescriptive feedback to flaws identified in the subject's and object's motion. Such feedback may be based on an exhaustive body of object motion correlations made during biomechanical research, and be provided to the user via the interactive interface.

The third element, the interactive interface, utilizes information generated by the physics engine to create a user-interface that displays data to the user. This interactive interface may be implemented in variety of forms such as mobile device screens (iOS/Android), Web-Based interfaces (HTML), Heads-Up-Displays (VR/AR Headsets), and Windows/OSX static formats (spreadsheets, PDF's, etc.). The interactive interface has the capability of feeding information to the user, as well as the ability to collect information from the user for the purpose of monitoring compliance and monitoring usability of the interface. The interactive platform may be utilized to provide to the user insight gathered from biomechanical research and marker-based motion capture methods. Such interactive platforms will be able to offer prescriptive feedback based on motion data gathered from either the wearable technology, or the motion sensing mechanism built into the interactive platform and enable compliance monitoring and continuous engagement across a suite of wearable technology methods. Information may be stored on a back-end storage server and also exported to the physic engine and to one or more of the hardware devices.

According to one aspect of the disclosure, system for providing prescriptive feedback based on motion of a human subject or object comprises: A) a hardware engine for gathering data about the motion of a subject or object, B) a physics engine operatively coupled to the hardware engine and configured for processing the gathered motion data and correlating the processed motion data with previously stored biomechanical data representing idealized motion models, and C) an interactive interface operatively coupled to the data gathering devices and the physics engine and configured for providing prescriptive feedback on flaws identified in the subject's or object's motion.

According to another aspect of the disclosure, a method for providing prescriptive feedback based on motion of a human subject or object comprises: A) gathering data about the motion of a subject or object, B) processing the gathered motion data and correlating the processed motion data with previously stored biomechanical data representing idealized motion models, and C) providing prescriptive feedback on flaws identified in the subject's or object's motion. In one embodiment method further comprises D) enabling compliance monitoring of the motion of the subject and/or object.

According to yet another aspect of the disclosure, a method for offering prescriptive feedback based on motion of a human subject and/or objects comprises: A) gathering motion data from either a wearable garment or device having motion sensing hardware embedded therein or from a motion sensing mechanism built into the interactive platform, B) processing motion data, C) correlating the process motion data with previously stored biomechanical data representing idealized motion models, and D) providing prescriptive feedback on flaws identified in the subject's and object's motion based on the motion data gathered from either the wearable technology or interactive platform.

BRIEF DESCRIPTION OF THE DRAWINGS

The present disclosure is illustratively shown and described with reference to the accompanying drawing in which:

FIG. 7 illustrates conceptually a diagram of an exemplary computer architecture in accordance with the present disclosure.

DETAILED DESCRIPTION OF THE INVENTION

The present disclosure will be more completely understood through the following description, which should be read in conjunction with the drawings. In this description, like numbers refer to similar elements within various embodiments of the present disclosure. The skilled artisan will readily appreciate that the methods, apparatus and systems described herein are merely exemplary and that variations can be made without departing from the spirit and scope of the disclosure.

Is used herein, the term "engine" means one or more elements, whether implemented in hardware, software, firmware, or any combination thereof, capable of performing any function described herein, including a collection of such elements which collaboratively perform functions wholly or partially, serially or in parallel, synchronously or asynchronously, remotely or locally, regardless of data formats or protocols.

Figure 1:
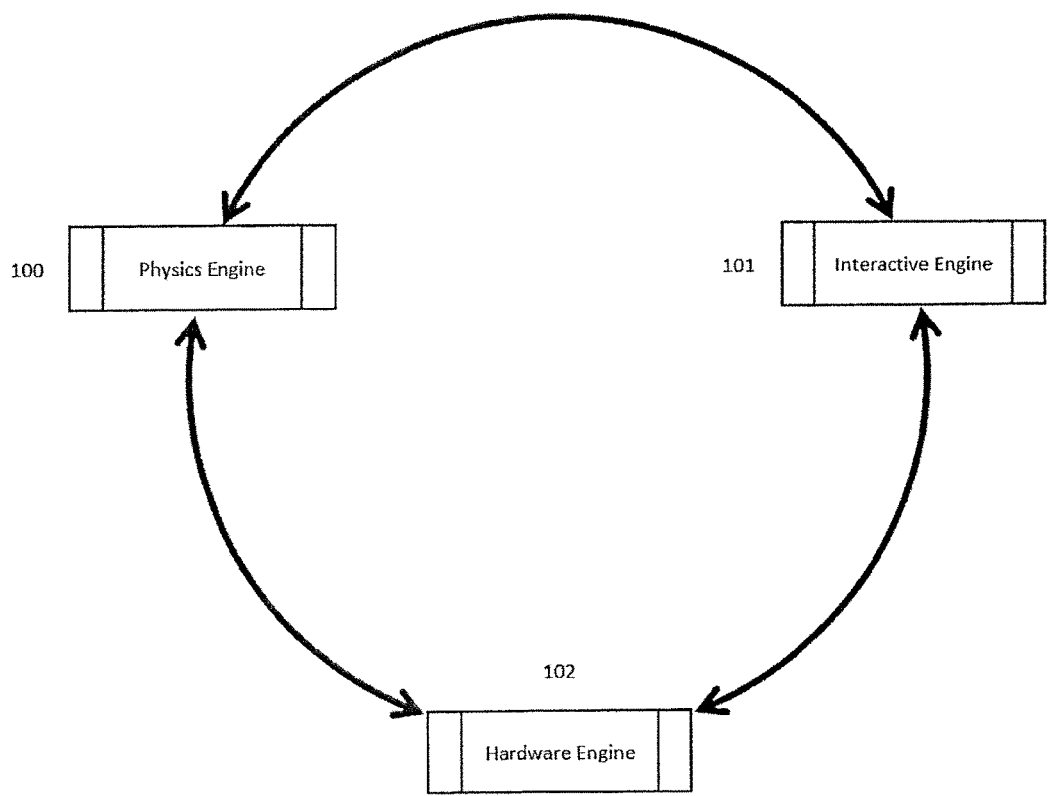
FIG. 1 illustrates conceptually a system for delivering biomechanical feedback to human and object motion.

Referring to FIG. 1, a system for providing biomechanical feedback comprises a physics engine 100, a hardware engine 102, and an interactive engine 101 to deliver biomechanical feedback on human or object motion. As used herein, hardware engine 102 may comprise one or a plurality of hardware/software devices which function collectively or individually to achieve the described functionality. Similarly, as used herein, interactive engine 101 may comprise one or a plurality of hardware/software devices which function collectively or individually to achieve the described functionality, typically receiving data from or providing data to a subject.

Figure 2:
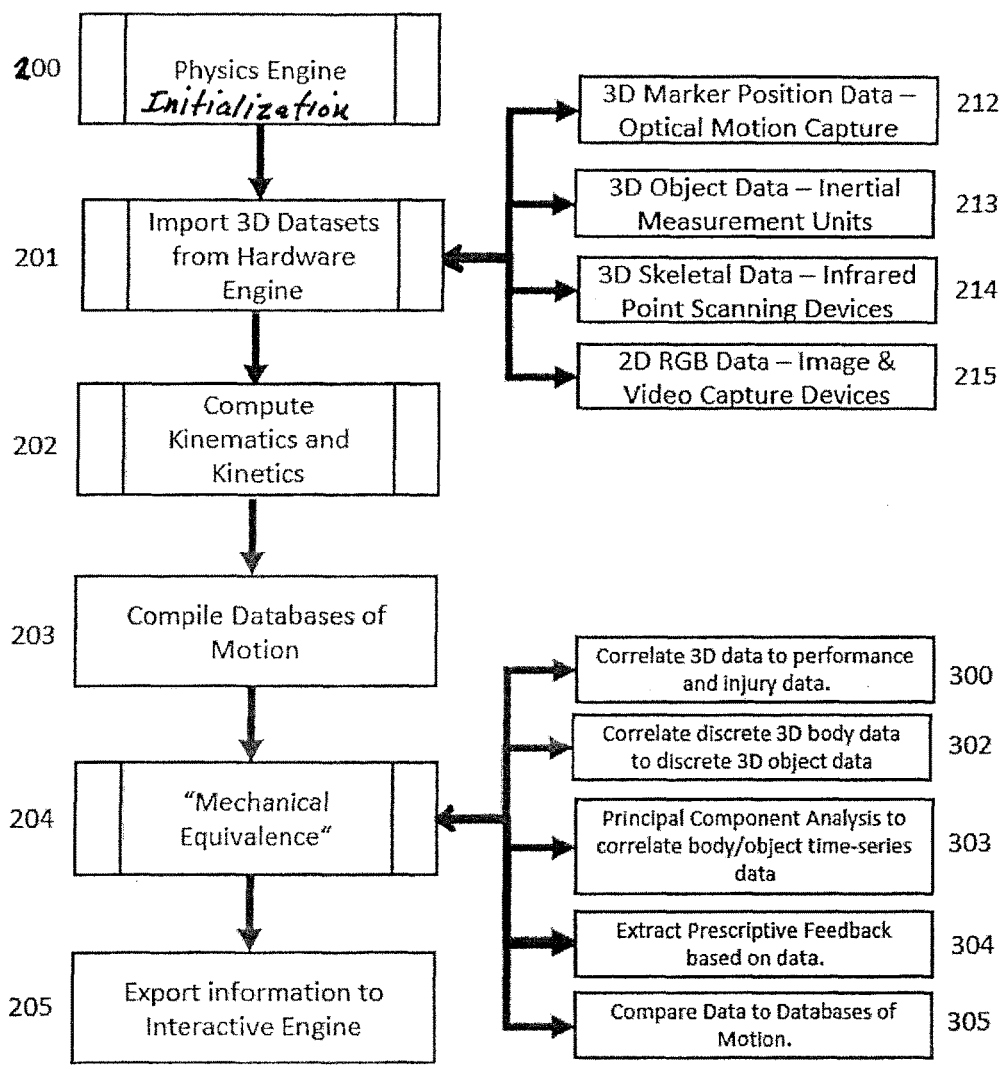
FIG. 2 illustrates conceptually a method of the system for delivering biomechanical feedback to human and object motion and the interaction of the physics engine.

Physics engine 100 functions as a cross-platform compatible method to transform raw three-dimensional data captured from various hardware data collection devices into usable biomechanical feedback. FIG. 2 illustrates conceptually an exemplary process flow of the physics engine 100. First, the physics engine 100 is initialized, typically to a startup state with default parameters, as illustrated by process block 200. The physics engine 100 imports, either in a push or a pull manner over any network infrastructure, wireless or otherwise, either two-dimensional or three-dimensional datasets from the hardware engine 102, as illustrated by process block 201. In one embodiment, hardware engine 102 may comprise individually or collectively any of optical motion capture device 212, inertial measurement units 213, infrared from point scanning devices 214, and image capture devices 215. Data imported from these devices is provided to physics engine 100 which performs one or more algorithmic processes to compute kinematics and kinetics of the human body and objects, as illustrated by process block 202.

An pseudocode example of the type of kinematic and kinetic algorithmic computations performed by physics engine 11 on data from optical motion capture device 212, infrared scanning devices 214 and image and video capture devices 215, is as follows:

- Define a multisegment or single segment biomechanics model comprising bilateral and/or unilateral segments, such as the hands, forearms, upper arms, upper trunk, neck, head, pelvis, upper thighs, lower shanks, feet, and any objects used in the proximity
- Define long-axis unit vectors of the body or object segments in the model using three-dimensional XYZ marker data
- Define Planar-axis unit vectors of each of the above segments
- Compute a cross product of the long and planar axes to determine the third unit vector of each segment
- Compute the cross product of the third unit-vector and the long-axis unit vector to create three orthonormal unit vectors for each segment in the model
- Compute angular velocity vectors of each model segment using a derivative method of unit vectors of each segment
- Compute relative joint angles (in euler and polar coordinate systems) using each segment's set of unit vectors
- Define human mass model using subject weight and height and anthropometrics of body segments to calculate mass moments of inertia about each segment, and center of mass locations
- Compute accelerations of each marker and of each segment center of mass using a five-point central difference filter
- Compute angular accelerations of each model segment using a five point central difference filter of angular velocity
- Compute an inverse dynamics model of motion using angular velocity components of each segment, angular acceleration components of each segment, and linear acceleration components of each segment's center of mass
- Event detection algorithms are used to determine points of interest during a particular motion
- Kinematics and Kinetic values are extracted at points of interest (examples of kinematics and kinetic values are peak angular velocity of the pelvis segment during a sport motion (in meters per second), or shoulder rotation at foot contact during a throwing motion (in degrees)

To compute kinematics and kinetics from inertial measurement units 213, the following steps are undertaken:

- Raw sensor data is fused together using an axis-angle integration method.
  - A rotation matrix of the sensor is initialized using the gravity vector during a still point (Gravity can also be detected when there is no still point by measuring integration offset after the axis-angle method is completed)
  - Angular rate data from the gyroscope is integrated into a rotation matrix at each sample during the motion
  - Each rotation matrix from each sample is multiplied consecutively to the initialized rotation matrix in a body-fixed method
  - Acceleration data is transformed into the global frame using the rotation matrix computed from the angular rate data
  - Gravity is subtracted from the rotated acceleration data in the global reference frame
  - Rotated acceleration data is integrated into velocity and position of the sensor and/or any point on a rigid body to which the sensor is attached
- Raw acceleration and angular rate data is transformed into the inertial reference frame at the center of mass of the segment or object to which the sensor is attached
- All processed data is rotated by an offset error that may exist in a system
- All rotated and inertial data is filtered using a fourth order low pass filter
- Inertial reference frame acceleration data and angular rate data are fed into an open-chain inverse dynamics kinetic model to solve for reaction forces and torques about vertices within a human or object mass model defined by anthropometrics, height, weight, or lookup tables of object properties
- Event detection algorithms are used to determine points of interest during a particular motion (An example of an event detection algorithm in baseball pitching encompases the generation of Principal Components of a historical dataset (training data). When a given buffer of data in a hardware device meets the criteria of fitting the principal components, an event (such as a pitch) is detected. Event detection is used to prevent undesired motion from being detected in a given application).
- Kinematics and Kinetic values are extracted at points of interest from integrated positions, velocities, accelerations, angular rates, and reaction force and torque data.

The above identified process for the computation of kinematics and kinetics data are repeated for multiple trials of a subject's or object's motion and compiled in a memory or database, as illustrated by process block 203. In one embodiment, similar computed kinematics and kinetics data are compiled across multiple subjects and stored for further analysis, as also illustrated by process block 203. Physics engine 100 then provides relevant portions of the compiled kinematics and kinetics data to mechanical equivalency models, as illustrated by process block 204. As part of this process, physics engine 100 correlates the compiled data to performance and injury data, as illustrated by process block 300. Discrete data are correlated to performance and injury data by way of person correlations and Bayesian mixed regression to eliminate non-contributing factors. Physics engine 100 further correlates discrete kinematics and kinetics data of the body to discrete kinematics and kinetics of the object or other body segments, as illustrated by process block 302. Discrete body data are correlated other discrete body and object data 302 in a similar method to 300 by way of person correlations and Bayesian mixed regression. Also as part of this process, physics engine 100 correlates time-series data of the body to time-series data of other body parts or objects using principal component analysis, as illustrated by process block 303. Time-series segment data are reduced to multiple, e.g. over 80, principal components. The reduced components are then correlated to principal components of other body or object segments and are used to extract additional motion given raw data from one or more body segments. Discrete and time-series data are compared to a database of motion, as illustrated by process block 305, by use of averages and standard deviations of data across multiple subjects. Based upon relationships established during process blocks 300, 302, 303, 305, physics engine 100 further extracts prescriptive feedback using correlation models and the subject's/object's motion, as illustrated by process block 304. After the prescriptive feedback information is gathered by the physics engine 100, the prescriptive feedback is exported to interactive engine 101, as illustrated by process block 205, and presented to the subject/object in a matter that facilitates altering the mechanics in a way that leads to increased performance or reduced risk of injury.

Figure 3:
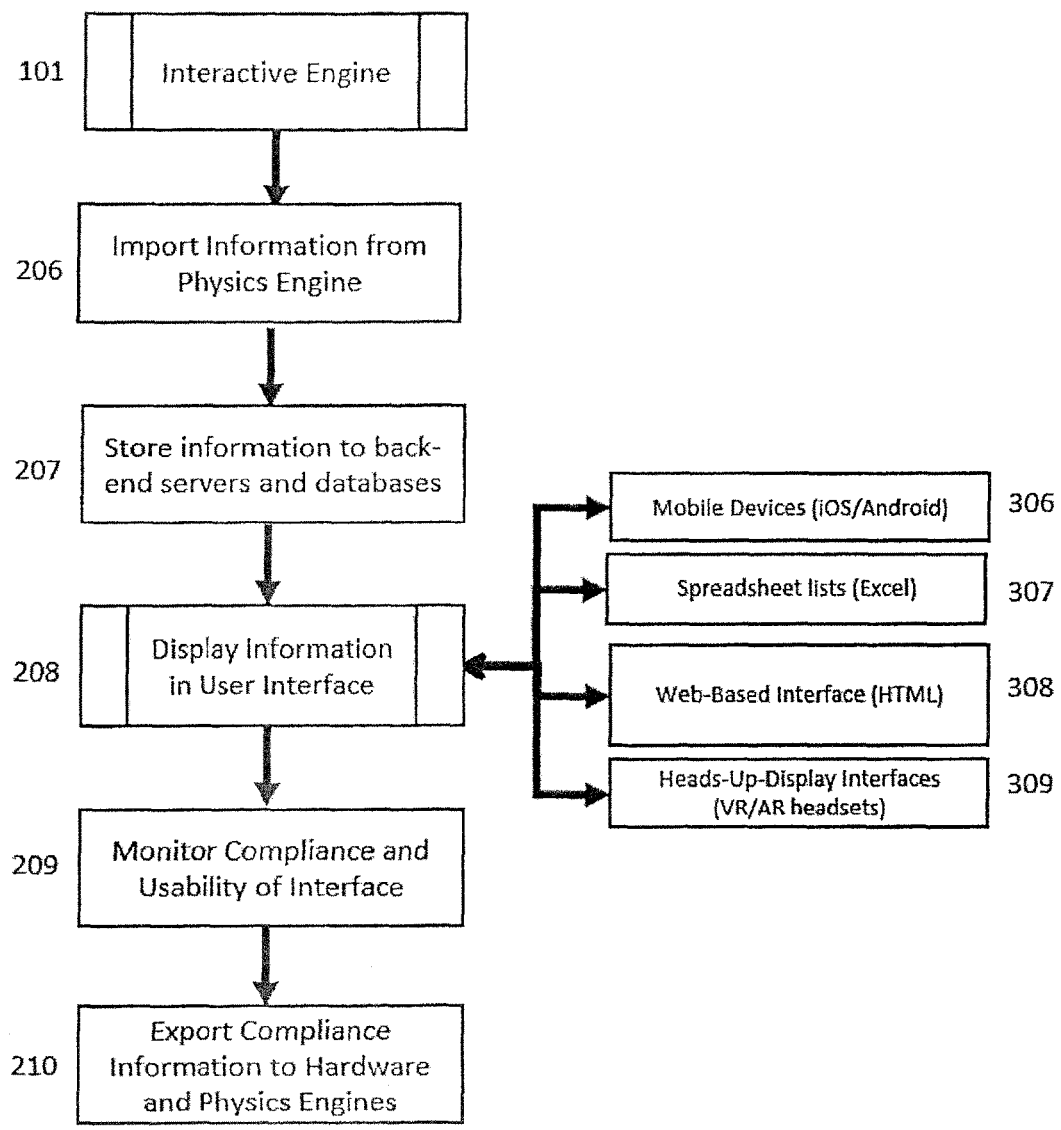
FIG. 3 illustrates conceptually a method of the system for delivering biomechanical feedback to human and object motion by use of an interactive engine.

FIG. 3 illustrates the process flow performed by the interactive engine 101. After any initialization of the interactive engine 101, information is acquired from the physics engine 100, as illustrated by process block 206, either manually, or with automated API's in either a push or pull protocol. Such information is then stored on back end servers and databases, as illustrated by process block 207, in a logical manner for reference. Next, the information acquired from physics engine 100 is displayed through user interfaces, as illustrated by process block 208. Interactive engine 101 may display the information acquired from physics engine 100 through any of mobile devices (iOS/Android) 306, spreadsheets 307, web-based interfaces (HTML) 308, and virtual and/or augmented reality heads-up displays 309, as illustrated by process block 208. After such information is displayed, the interactive engine 101 has the further capability to monitor compliance and usability information through the various interface components of interactive engine 101, as illustrated by process block 209, by storing compliance information entered by a user or collected by one of the data collection devices comprising hardware engine 102. Any acquired compliance information may be exported to either the hardware engine 102 and/or physics engine 100, as applicable, to form a continuous feedback loop, as illustrated by process block 210, and as illustrated in FIG. 1.

Figure 4A:
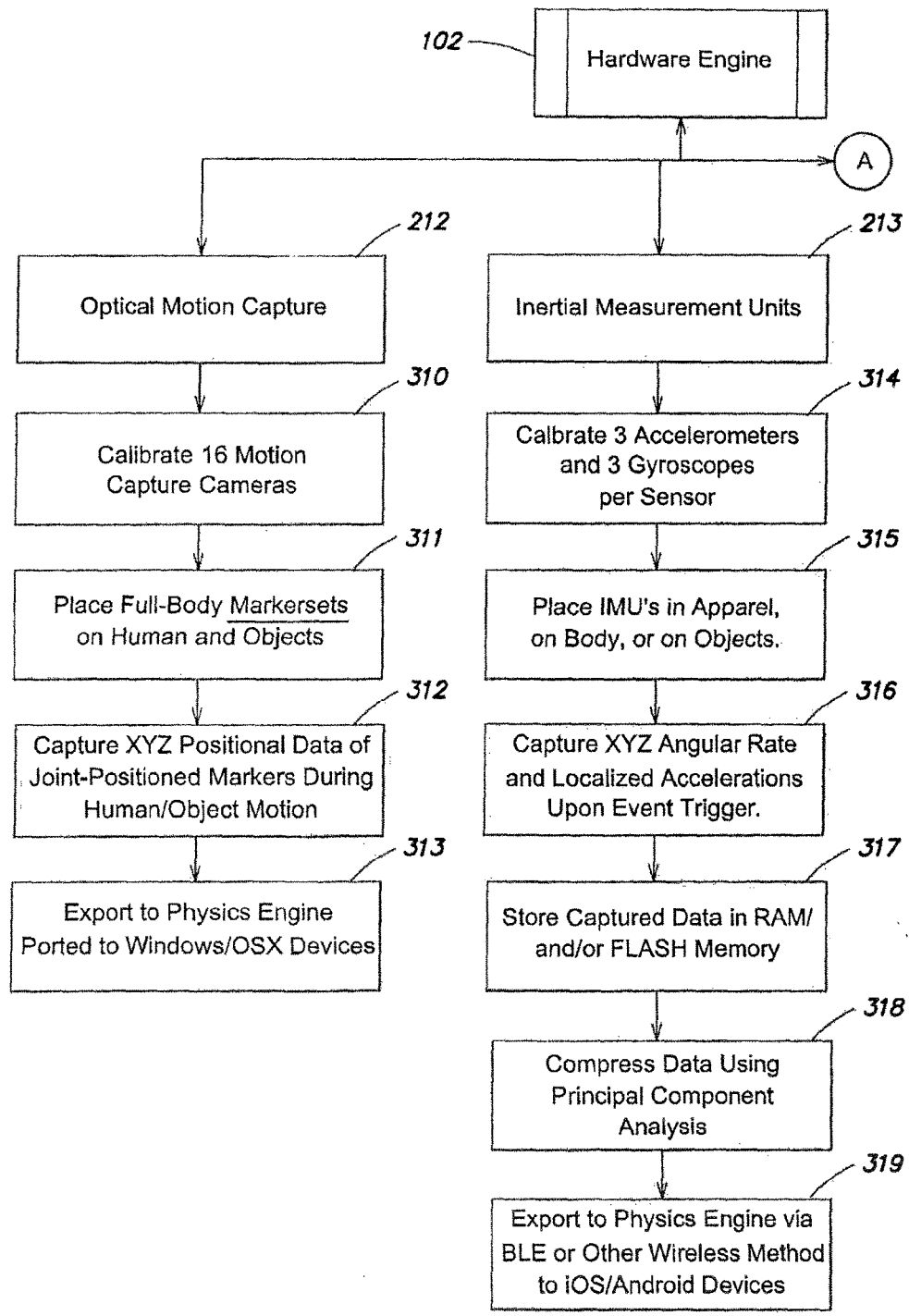
FIG. 4A-B illustrate conceptually a method of the system for delivering biomechanical feedback to human and object motion by use of hardware engines.
Figure 4B:
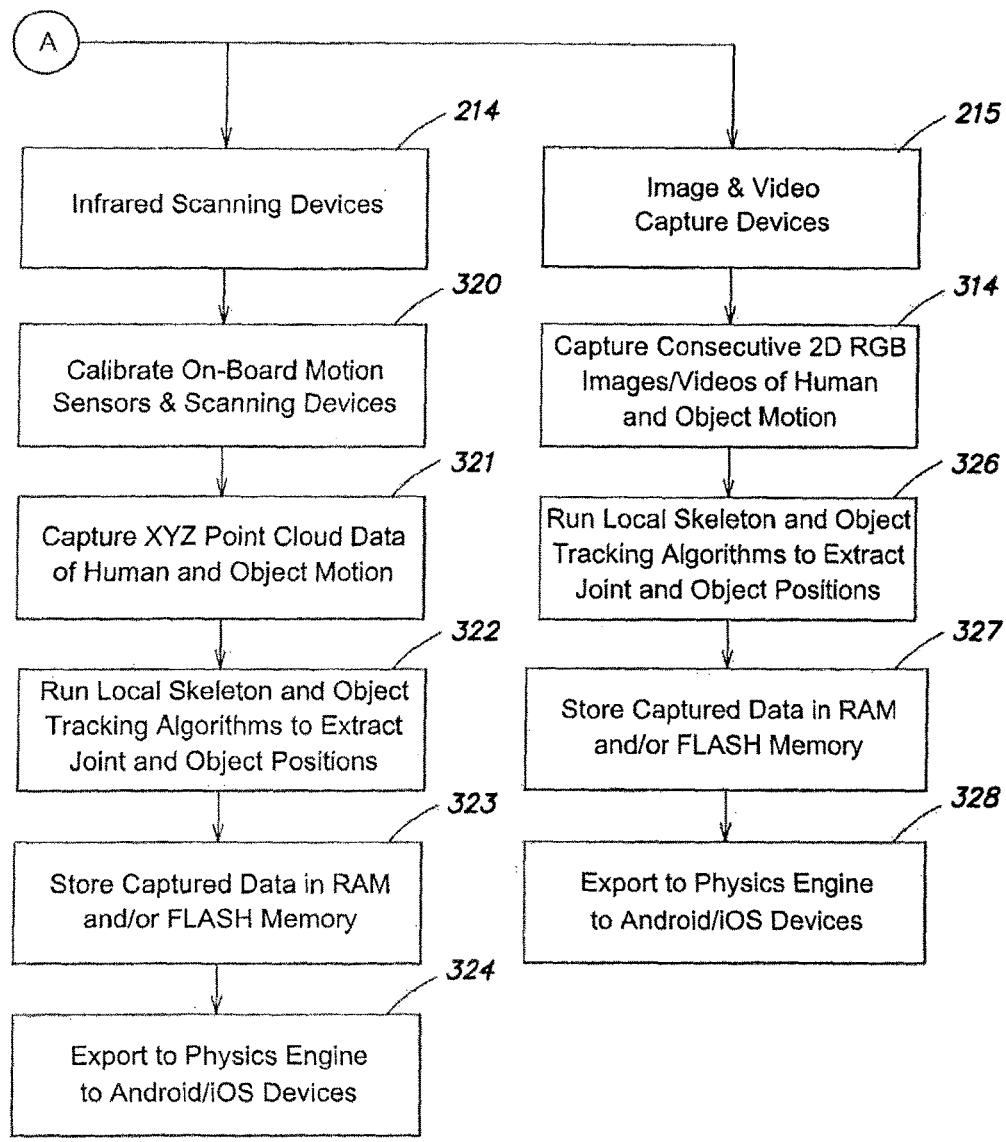

FIGS. 4A-B illustrate the process flow performed by the hardware engine 102. For the optical motion capture devices 212, third party software is utilized to calibrate multiple, e.g. up to 16, near infrared cameras around a centralized volume space, as illustrated by process block 310. Retro-reflective markers are then placed on the subject and/or object as seen in FIGS. 5A-D. Data are recorded with devices 212 and transmitted using an Ethernet bus connected to a computer. The calibrated XYZ positions of each marker in the capture volume are recorded into a binary encoded file, as illustrated by process block 312. After collection, the acquired data are exported to the physics engine 102, for example using Windows/OSX devices, for processing, as illustrated by process block 313. For the inertial measurement devices 213, accelerometers and gyroscopes are calibrated and interfaced with a microcontroller capable of interfacing with any of memory, e.g. RAM or FLASH, and Bluetooth chipsets by internal firmware operations that control the hardware, as illustrated by process block 314. Inertial measurement units are placed on points of interest, such as body segments or objects, as illustrated by process block 315. Six axes of data, in addition to time samples, may be recorded continuously. Upon the trigger of a customized event (event detection), as illustrated by process block 316, data are stored in RAM and/or FLASH memory for later analysis, as illustrated by process block 317. Data are simultaneously compressed using principal component analysis, similar as previously described with reference to process block 303, as illustrated by process block 318. Data are then exported to a physics engine 100, with, for example, Bluetooth low energy SDK processes on mobile devices (iOS/Android), as illustrated by process block 319. For the infrared scanning devices 214, a scanning laser is calibrated alongside on-board inertial measurement units that may include accelerometers and gyroscopes, or other positional measurement units, such as Red Green Blue (RGB) video or known environmental conditions, as illustrated by process block 320. XYZ point cloud data of human and object motion is then captured, as illustrated by process block 321, and stored to local memory. Simultaneously, a local skeletal and object tracking algorithm is implemented to track three-dimensional joint and object positions, as illustrated by process block 322. The local skeletal and object tracking algorithm may be implemented using known anthropometrics of the human, or known information from the object, alongside edge filtering techniques to identify points of interest on a human or object. Skeletal and object data are then also stored in memory, as illustrated by process block 323, and are exported to a physics engine 100 by, for example, Android/iOS devices. For the image and video capture devices 215, consecutive two-dimensional RGB images and videos of human object motion are captured, as illustrated by process block 325. A local skeleton and object tracking algorithm is then used to extract joint and object positions similar as previously described with reference to process block to 322, as illustrated by process block 326. Skeletal and object positional data are then stored to memory, as illustrated by process block 327, and are exported to physics engine 100, by for example, mobile devices (iOS/Android), as illustrated by process block 328.

Figure 5A:
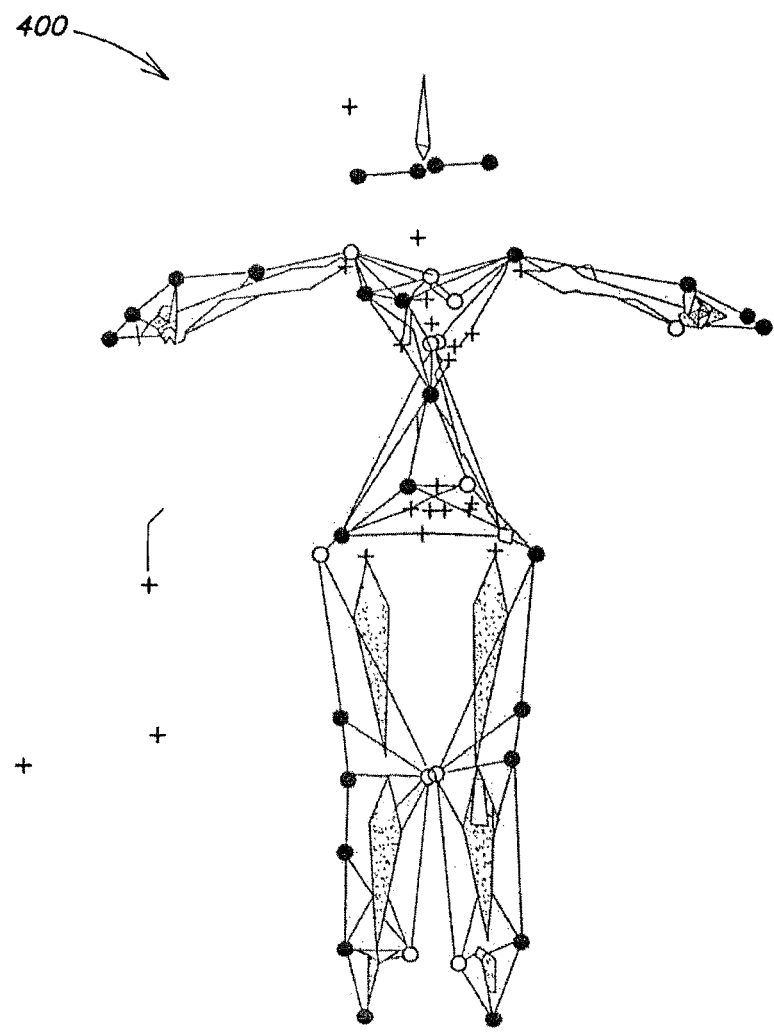
FIGS. 5A-D illustrate conceptually specific marker sets used in the method of biomechanical research and its relation to optical motion capture.

As seen in FIG. 5A-D, markerset 300 comprise a full body markerset 400 and various object markersets, including baseball/softball bat markerset 401, golf clubs markerset 402, tennis racket markerset 403, and other objects that interact with a human body. FIG. 5A illustrates conceptually a full body markerset 400 comprises markers attached to bony anatomical landmarks, including, but not limited to: front of the head, back of the head, right side of the head, left side of the head, the T2 vertebrate, the T8 vertebrate, the Xiphoid process of the sternum, the left and right sternoclavicular joints, the Acromioclavicular joint of both shoulders, the middle of the bicep of the upper arms, the lateral and medial epicondyle of both humeruses, middle of the forearms, the medial and lateral styloid processes of both wrists, the tip of the third metacarpal in both hands, the right and left posterior superior iliac spines, the right and left anterior superior iliac spines, the right and left greater trochanters, the middle of both thighs, the medial and lateral epicondyles of the femurs, the right calf, the medial and lateral malleouleses of the ankles, the tip of the third metatarsal of both feet, and the tip of the calcaneous in both feet.

Figure 5D:
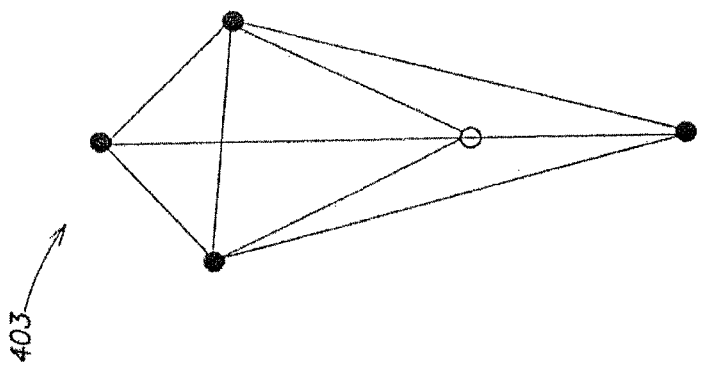
Figure 5C:
Figure 5B:

FIG. 5B illustrates conceptually a markerset 401 with five markers attached to a hypothetical baseball bat in the following locations: knob of bat, above the handle of the bat, at the center of mass of the bat, at the tip of the bat forming a line between the knob and center of mass, and on the posterior side of the bat at the tip.

FIG. 5C illustrates conceptually a markerset 402 with five markers attached to a hypothetical golf club at the following locations: at the base of the handle, above the handle, at the center of mass, at the base of the club, and at the tip of the clubface to form a direct line of the clubface angle.

FIG. 5D illustrates conceptually a markerset 403 with five markers are placed on a hypothetical tennis racket at the following locations: at the base of the handle, at the intersection of the handle and the racket head, on the left and right sides of the racket head, and at the tip of the racket head.

Referring to FIGS. 6A-H, wearable technology 102, they comprise in embodiments any of a plurality of garments 800, which may be made of any material including spandex, Lycra, polyester, in combination with cotton, silk or any other wearable material, to assist with the acquisition of motion data from human subjects and/or accompanying objects. Various embodiments of such garments are described in greater detail below. Each garment 800 comprises multiple data-gathering mechanisms 801, such as MEMS/IMU hardware, which can which can record and transmit motion data wirelessly to an iOS/Android phone or other network enabled device 802. Software applications, such as those available from Diamond Kinetics, Pittsburgh, Pa. may be utilized to compute kinematics from MEMS/IMU hardware.

Figure 6A:
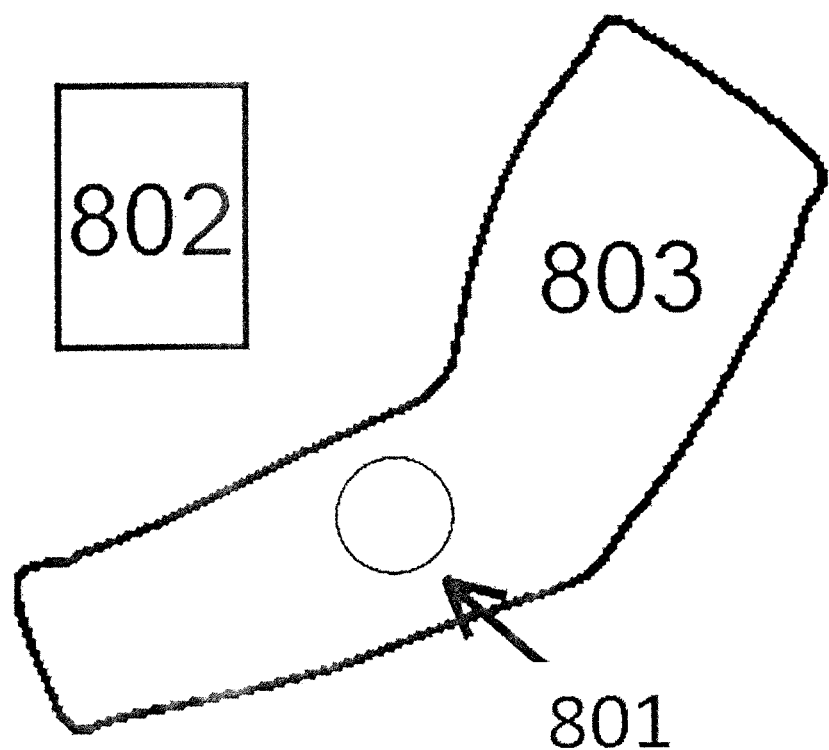
FIGS. 6A-H illustrate conceptually embodiments of wearable technology in accordance with the disclosure.

In one embodiment, the mThrow sleeve garment 803, as illustrated in FIG. 6A, is coupled with motion sensors 801 to monitor workload and performance. The mThrow sleeve garment 803 is worn on the throwing arm during practices, games, or rehab sessions. Data may be collected throughout workouts and is transmitted wirelessly to an iOS/Android phone or other network enabled device. In such embodiment, garment 803 may comprise 801 a six axis accelerometer/gyroscope IMU that interfaces wirelessly via Bluetooth or other protocol with a mobile device 802, such as an iOS/Android smartphone. Software applications, either executing on the network enabled device or remotely accessible via a network, perform the functions to interact with the physics engine 100 and interactive engine 101. Such existing functions include computation of throwing forearm motion, kinetic solutions of elbow reaction forces and torques, algorithmic calculation of throwing workload during game/practice/season/career, pitch and throw counting functions, computation of arm and ball speed, and trends for the use of performance and injury forecasting. Principal component analysis of sensor data will also allow for mechanical equivalence models to be created that extract additional segment data that is not directly measured by the sensors.

Figure 6B:
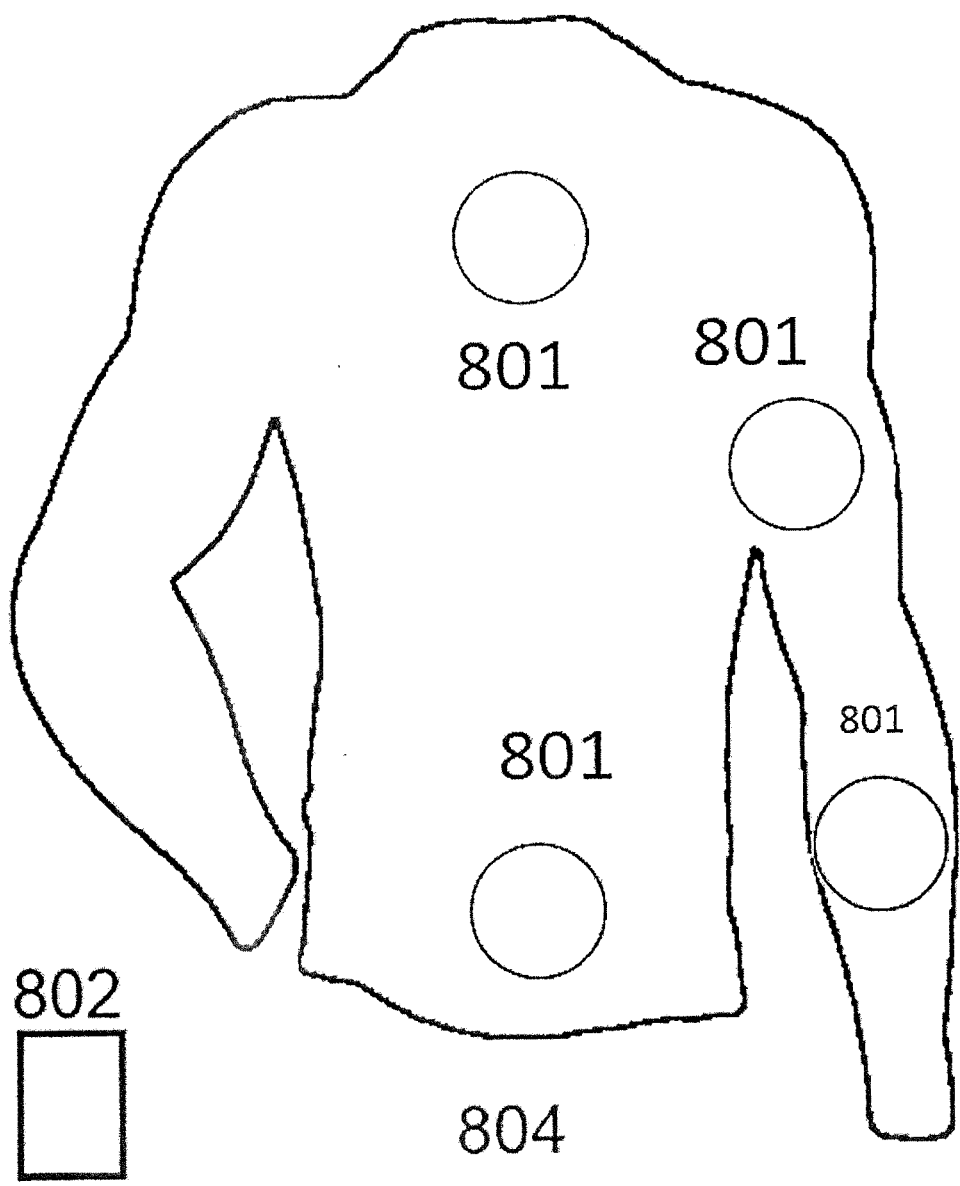

In another embodiment, the mThrow Pro garment 804, as illustrated in FIG. 6B, is a comprehensive throwing analysis platform designed to allow athletes of all ages and skill level to receive a full-body biomechanical analysis of their throwing mechanics. Data is gathered with four motion sensors. mThrow Pro garment 804 can be worn during games or practices, and is coupled with interactive applications to provide useful feedback. In such embodiment, garment 804 may comprise 801 multiple six axis accelerometer/gyroscope IMU's that interfaces wirelessly via Bluetooth or other protocol with a mobile device 802, such as an iOS/Android smartphone. Software applications, either executing on the network enabled device or remotely accessible via a network, perform the functions to interact with the physics engine 100 and interactive engine 101. Such existing functions include computation of throwing forearm, upper arm, pelvis, and upper trunk biomechanical motion, kinetic solution of elbow and shoulder reaction forces and torques, algorithmic calculation of throwing workload during game/practice/season/career, pitch and throw counting functions, computation of ball and arm speed, computation of kinetic chain velocities and accelerations of the pelvis, upper trunk, upper arm, and forearm and their associated temporal reference, and trends for the use of performance and injury forecasting. Principal component analysis of sensor data will also allow for mechanical equivalence models to be created that extract additional segment data that is not directly measured by the sensors.

Figure 6C:
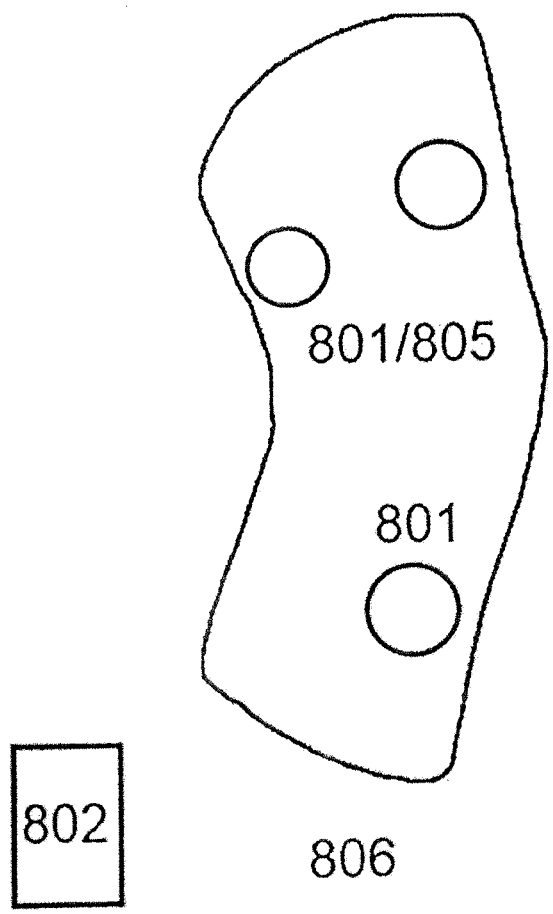

In another embodiment, the mRun ACL Sleeve garment 806, as illustrated in FIG. 6C, is coupled with motion sensors 801 and EMG muscle activity sensors 805 to detect injury risk factors and workload in athletic movements such as running, sprinting, cutting, and jumping. The mRun ACL Sleeve garment 806 can be used on the field of play during games, practice, or training. The mRun ACL Sleeve garment 806 may comprise 801 a six axis accelerometer/gyroscope IMU and 805 two EMG sensors on the quadriceps and hamstrings that interfaces wirelessly via Bluetooth or other protocol with a mobile device 802, such as an iOS/Android smartphone. Software applications, either executing on the network enabled device or remotely accessible via a network, perform the functions to interact with the physics engine 100 and interactive engine 101. Such existing functions include computation of lower extremity kinematics, muscle firing activity, and algorithmic computation of movement workload during game/practice/season/career, and trends for the use of performance and injury forecasting. Principal component analysis of sensor data will also allow for mechanical equivalence models to be created that extract additional segment data that is not directly measured by the sensors.

Figure 6D:
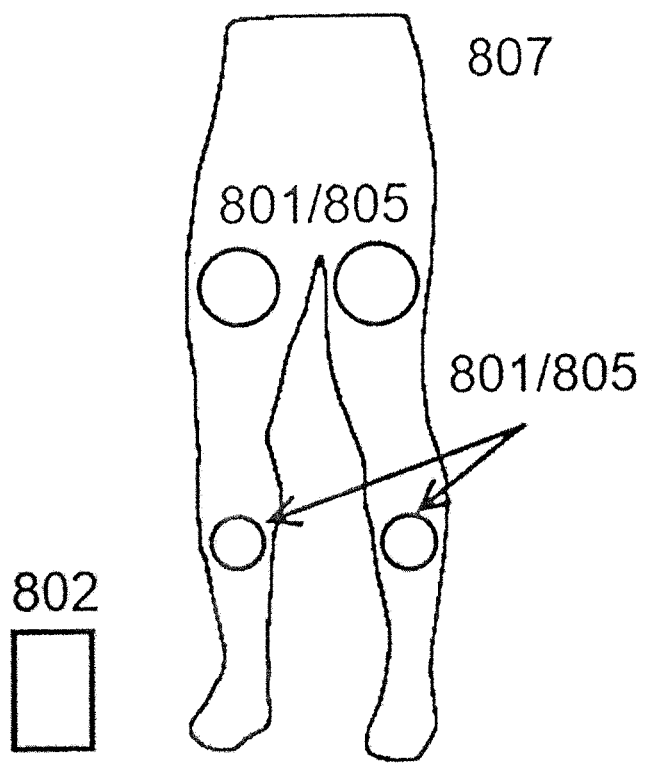

In another embodiment, the mRun ACL Leggings Pro garment 807, as illustrated in FIG. 6D, give athletes in any sport the ability to reduce their risk of injury and enhance performance. Garment 807 is a comprehensive movement analysis platform that captures ACL injury risk. The mRun ACL Leggings Pro garment 807 uses motion sensors 801 and muscle activity sensors 805 to monitor the entire lower body during any movement. mRun ACL Leggings Pro garment 808 may be used during any training platform to allow athletes to undergo an ACL risk screening. In such embodiment, garment 808 may comprise 801 two six axis accelerometer/gyroscope IMU's and 805 six EMG sensors on the quadriceps, hamstrings, and gluteus medius that interfaces wirelessly via Bluetooth or other protocol with a mobile device 802, such as an iOS/Android smartphone. Software applications, either executing on the network enabled device or remotely accessible via a network, perform the functions to interact with the physics engine 100 and interactive engine 101. Such existing functions include computation of full lower extremity kinematics and kinetics, computation of full lower extremity muscle firing activity, algorithmic computation of movement workload during game/practice/season/career, and the use of performance and injury forecasting. Principal component analysis of sensor data will also allow for mechanical equivalence models to be created that extract additional segment data that is not directly measured by the sensors.

Figure 6E:
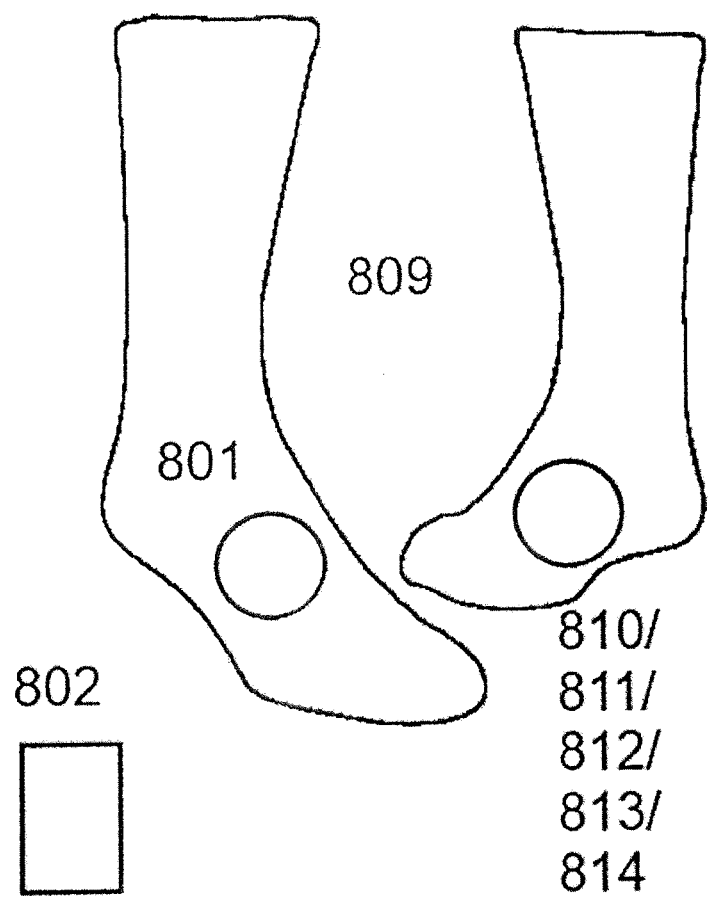

In another embodiment, the SmartSocks garment 809, as illustrated in FIG. 6E, can be used in any sport to monitor feet movement, running patterns, and weight distribution. Coupled with force sensor arrays and motion sensors, the SmartSocks garment 810 can interface with any of the garments disclosed herein to provide a more comprehensive experience. In such embodiment, garment 810 may comprise 801 a six axis accelerometer/gyroscope IMU that interfaces wirelessly via Bluetooth or other protocol with a mobile device 802, such as an iOS/Android smartphone. Software applications, either executing on the network enabled device or remotely accessible via a network, perform the functions to interact with the physics engine 100 and interactive engine 101. Additional sensor technology is to include 810 cardiac sensor for heart rate and respiration rate measurement, 811 blood oxygenation sensor, 812 sweat and hydration sensors, 813 global positioning system sensors for on field movement monitoring, and 814 force sensor arrays for weight distribution and lower extremity kinetic computations. Together, these elements will allow for in depth analysis of player workload during practice and games, while offering performance alerts in the form of dashboards for forecasting performance and injury. The embodiment 809 will also have the capability to pair sensor data with 800 804 806 807.

Figure 6F:
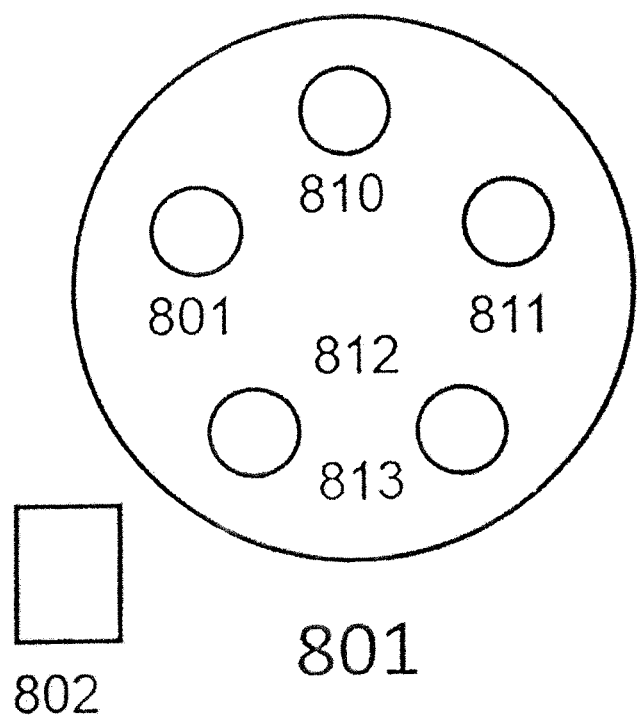

In another embodiment, the mSense device 801, as illustrated in FIG. 6F, comprises 801 motion sensors, 810 cardiac heart and breathing monitors, 811 oxygen sensors, 812 sweat and hydration sensors, and 813 GPS to monitor team members during gameplay, practice, and training sessions. The mSense device 801 is designed for the competitive individual as well as for coaches to monitor their entire team and embeds in on to any garment and interfaces wirelessly with your phone 802 with a user interface in the form of dashboards to monitor player workload. In such embodiment, device 801 may comprise of a six axis accelerometer/gyroscope IMU that interfaces wirelessly via Bluetooth or other protocol with 802 a mobile device, such as an iOS/Android smartphone. Software applications, either executing on the network enabled device or remotely accessible via a network, perform the functions to interact with the physics engine 100 and interactive engine 101.

Figure 6G:
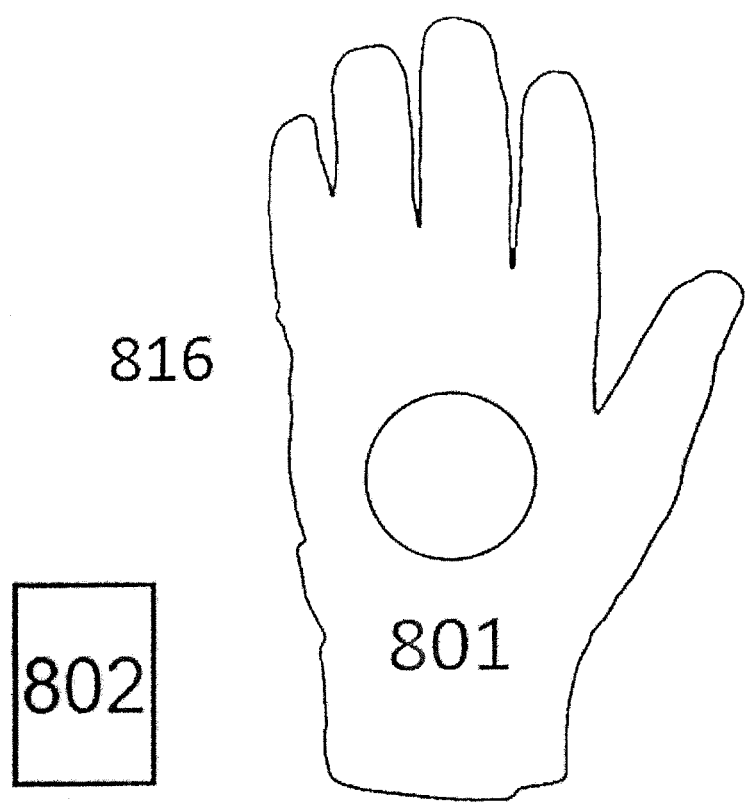

In another embodiment, the mSwing glove garment 816, as illustrated in FIG. 6G, is coupled with motion sensors 801 to monitor workload and performance of swinging motions such as but not limited to golf swings, baseball batting swings, softball batting swings, tennis swings, and lacrosse swings. The mSwing glove garment 816 is worn on the dominant and/or non-dominant arm during practices, games, or rehab sessions. Data may be collected throughout workouts and is transmitted wirelessly to an iOS/Android phone or other network enabled device. In such embodiment, garment 816 may comprise 801 a six axis accelerometer/gyroscope IMU that interfaces wirelessly via Bluetooth or other protocol with a mobile device 802, such as an iOS/Android smartphone. Software applications, either executing on the network enabled device or remotely accessible via a network, perform the functions to interact with the physics engine 100 and interactive engine 101. Such existing functions include computation of held object motion, kinetic solutions of wrist reaction forces and torques, algorithmic calculation of swinging workload during game/practice/season/career, swing counting functions, computation of held object speed, kinematics and temporal measures, and trends for the use of performance and injury forecasting. Principal component analysis of sensor data will also allow for mechanical equivalence models to be created that extract additional segment data that is not directly measured by the sensors.

Figure 6H:
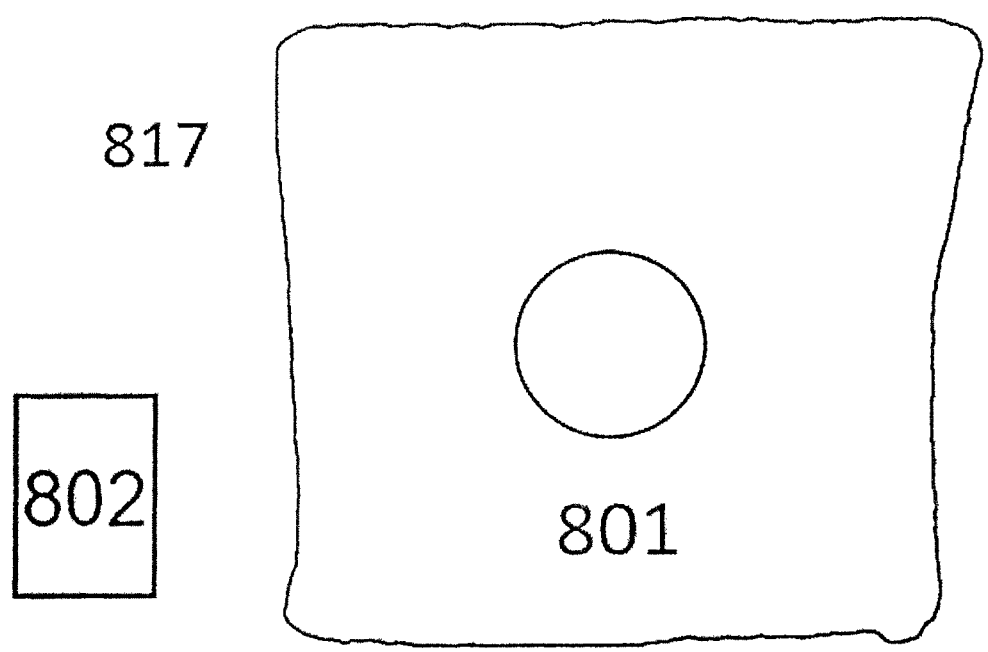

In another embodiment, the mBand wristband garment 817, as illustrated in FIG. 6H, is coupled with motion sensors 801 to monitor workload and performance of swinging motions such as but not limited to golf swings, baseball batting swings, softball batting swings, tennis swings, and lacrosse swings. The mBand wristband garment 817 is worn on the dominant and/or non-dominant arm during practices, games, or rehab sessions. Data may be collected throughout workouts and is transmitted wirelessly to an iOS/Android phone or other network enabled device. In such embodiment, garment 817 may comprise 801 a six axis accelerometer/gyroscope IMU that interfaces wirelessly via Bluetooth or other protocol with a mobile device 802, such as an iOS/Android smartphone. Software applications, either executing on the network enabled device or remotely accessible via a network, perform the functions to interact with the physics engine 100 and interactive engine 101. Such existing functions include computation of held object motion, kinetic solutions of wrist reaction forces and torques, algorithmic calculation of swinging workload during game/practice/season/career, swing counting functions, computation of held object speed, kinematics and temporal measures, and trends for the use of performance and injury forecasting. Principal component analysis of sensor data will also allow for mechanical equivalence models to be created that extract additional segment data that is not directly measured by the sensors.

The previously described physics engine 100 and the processes or functions performed thereby may be implemented with computer program code executing under the control of an operating system and running on one or more primary hardware platforms as described with reference to FIG. 7. Referring to FIG. 7, a computer system 500 comprises a central processing unit 502 (CPU), a system memory 530, including one or both of a random access memory 532 (RAM) and a read-only memory 534 (ROM), and a system bus 510 that couples the system memory 530 to the CPU 502. An input/output system containing the basic routines that help to transfer information between elements within the computer architecture 500, such as during startup, can be stored in the ROM 534. The computer architecture 500 may further include a mass storage device 520 for storing an operating system 522, software, data, and various program modules 600, associated with an application 580 which may include functionality described herein with reference to any of physics engine 100, hardware engine 102 or interactive engine 100, one or any combination thereof which are executable by a special-purpose application, such as analytics engine 524.

The mass storage device 520 may be connected to the CPU 502 through a mass storage controller (not illustrated) connected to the bus 510. The mass storage device 520 and its associated computer-readable media can provide non-volatile storage for the computer architecture 500. Although the description of computer-readable media contained herein refers to a mass storage device, such as a hard disk or CD-ROM drive, it should be appreciated by those skilled in the art that computer-readable media can be any available computer storage media that can be accessed by the computer architecture 500.

By way of example, and not limitation, computer-readable media may include volatile and non-volatile, removable and non-removable media implemented in any method or technology for the non-transitory storage of information such as computer-readable instructions, data structures, program modules or other data. For example, computer-readable media includes, but is not limited to, RAM, ROM, EPROM, EEPROM, flash memory or other solid state memory technology, CD-ROM, digital versatile disks (DVD), HD-DVD, BLU-RAY, or other optical storage, magnetic cassettes, magnetic tape, magnetic disk storage or other magnetic storage devices, or any other medium which can be used to store the desired information and which can be accessed by the computer architecture 500.

According to various embodiments, the computer architecture 500 may operate in a networked environment using logical connections to remote physical or virtual entities through a network such as the network 599. The computer architecture 500 may connect to the network 599 through a network interface unit 504 connected to the bus 510. It will be appreciated that the network interface unit 504 may also be utilized to connect to other types of networks and remote computer systems. The computer architecture 500 may also include an input/output controller for receiving and processing input from a number of other devices, including a keyboard, mouse, or electronic stylus (not illustrated). Similarly, an input/output controller may provide output to a video display 506, a printer, or other type of output device. A graphics processor unit 525 may also be connected to the bus 510.

As mentioned briefly above, a number of program modules and data files may be stored in the mass storage device 520 and RAM 532 of the computer architecture 500, including an operating system 522 suitable for controlling the operation of a networked desktop, laptop, server computer, or other computing environment. The mass storage device 520, ROM 534, and RAM 532 may also store one or more program modules. In particular, the mass storage device 520, the ROM 534, and the RAM 532 may store the engine 524 for execution by the CPU 502. The engine 524 can include software components for implementing portions of the processes described herein. The mass storage device 520, the ROM 534, and the RAM 532 may also store other types of program modules.

Software modules, such as the various modules within the engine 524 may be associated with the system memory 530, the mass storage device 520, or otherwise. According to embodiments, the analytics engine 524 may be stored on the network 599 and executed by any computer within the network 599. Databases 572 and 575, which may be used to store any of the acquired or processed data or idealized models, and/or kinematics and kinetic data described herein, such databases being coupled remotely to network 599 and network interface 504.

The software modules may include software instructions that, when loaded into the CPU 502 and executed, transform a general-purpose computing system into a special-purpose computing system customized to facilitate all, or part of, the techniques disclosed herein. As detailed throughout this description, the program modules may provide various tools or techniques by which the computer architecture 500 may participate within the overall systems or operating environments using the components, logic flows, and/or data structures discussed herein.

The CPU 502 may be constructed from any number of transistors or other circuit elements, which may individually or collectively assume any number of states. More specifically, the CPU 502 may operate as a state machine or finite-state machine. Such a machine may be transformed to a second machine, or specific machine by loading executable instructions contained within the program modules. These computer-executable instructions may transform the CPU 502 by specifying how the CPU 502 transitions between states, thereby transforming the transistors or other circuit elements constituting the CPU 502 from a first machine to a second machine, wherein the second machine may be specifically configured to manage the generation of indices. The states of either machine may also be transformed by receiving input from one or more user input devices associated with the input/output controller, the network interface unit 504, other peripherals, other interfaces, or one or more users or other actors. Either machine may also transform states, or various physical characteristics of various output devices such as printers, speakers, video displays, or otherwise.

Encoding of executable computer program code modules may also transform the physical structure of the storage media. The specific transformation of physical structure may depend on various factors, in different implementations of this description. Examples of such factors may include, but are not limited to: the technology used to implement the storage media, whether the storage media are characterized as primary or secondary storage, and the like. For example, if the storage media are implemented as semiconductor-based memory, the program modules may transform the physical state of the system memory 530 when the software is encoded therein. For example, the software may transform the state of transistors, capacitors, or other discrete circuit elements constituting the system memory 530.

As another example, the storage media may be implemented using magnetic or optical technology. In such implementations, the program modules may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. It should be appreciated that various other transformations of physical media are possible without departing from the scope of and spirit of the present description.

Figure 8:
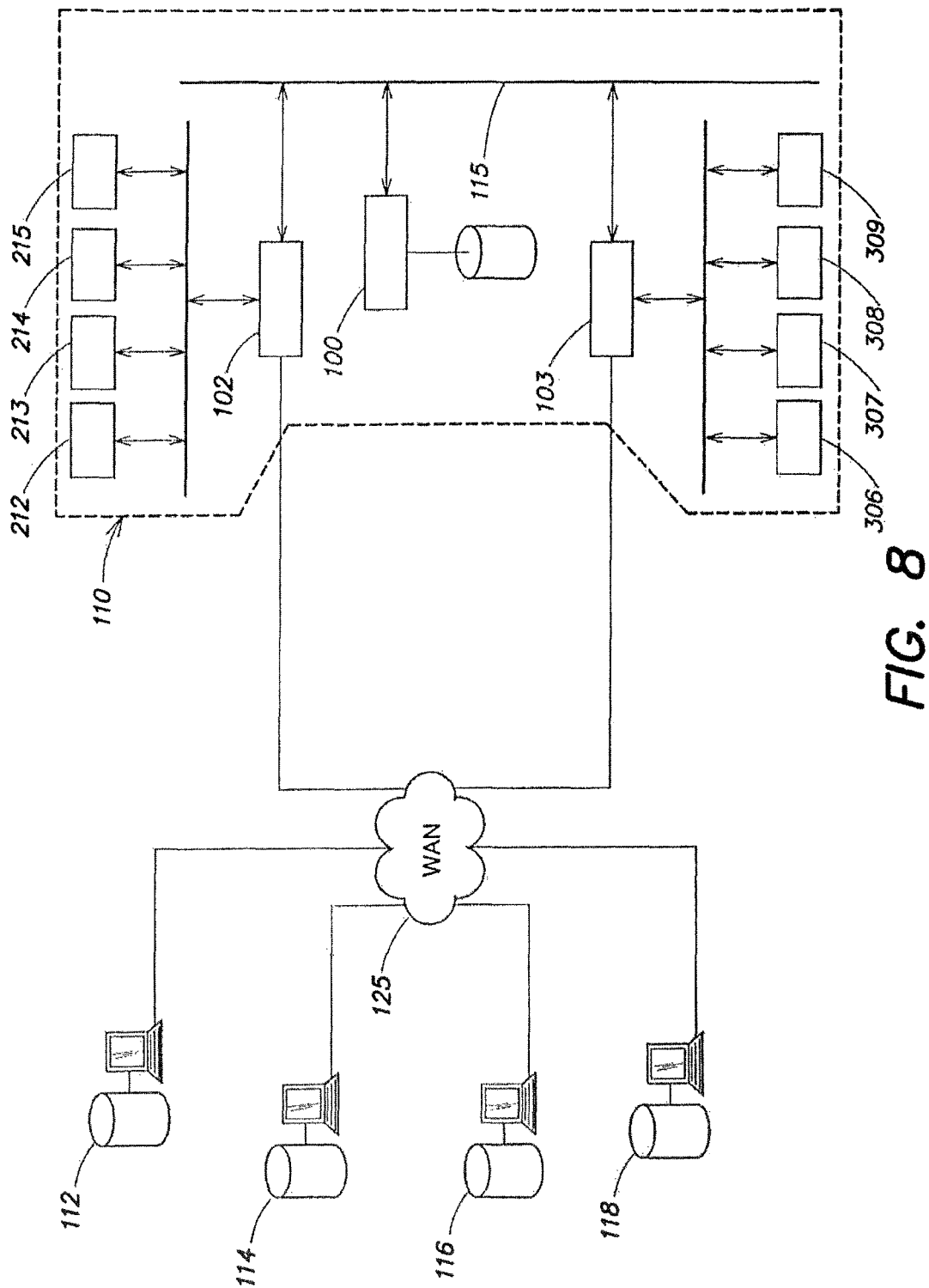
FIG. 8 illustrates conceptually a diagram of an exemplary network topology in which the system may be implemented in accordance with the present disclosure.

FIG. 8 illustrates conceptually a network topology in which the components of the disclosed system may be implemented. Any of the engines 100, 102 or 103 and the data processing systems 110, 113A-C, 112-118, illustrated in the network topology of FIG. 8 may be implemented with a processing architecture similar to that illustrated in FIG. 7, including any of a desktop computer, laptop computer, tablet computer or smart phone/personal digital assistant device such as an iPhone or android operating system based device. Note that any of the systems illustrated in FIG. 8 may be interoperably connected either through a wide area network (WAN) 125 or local area network (LAN) 115 or both, or any hybrid combination thereof using known network infrastructure and components, protocols, and/or topologies. For example, any of devices 212-215 may be connected to hardware engine 102 either through a physical network physically or wirelessly, or any combination thereof. Similarly any of devices 306-309 may be coupled to interface engine 103 either through a physical network or wirelessly, or any combination thereof. Similarly any of engines 100, 102, 103 may be connected either via WAN 125 or LAN 115, any portion of which may be wireless connection between respective network nodes, the entirety of the system being indicated as system 110. Systems 112-118 may comprise additional databases more users capable of interacting remotely with system 110.

The reader can appreciate that the various systems and elements and methods described herein enables delivery of near real-time feedback to motions of human subjects and any objects in their possession and proximity.

Although the various embodiments of the system and techniques disclosed herein have been described with reference to specific sports and/or garments related to such activities, it will be obvious to those reasonably skilled in the art that modifications to the systems and processes disclosed herein may occur, without departing from the true spirit and scope of the disclosure. For example, any type of wearable garment which is capable of transmitting motion data useful for analysis may be utilized with the systems and techniques described herein. Further, notwithstanding the network implementation described, any existing or future network or communications infrastructure technologies may be utilized, including any combination of public and private networks. In addition, although specific algorithmic flow diagrams or data structures may have been illustrated, these are for exemplary purposes only, other processes which achieve the same functions or utilized different data structures or formats are contemplated to be within the scope of the concepts described herein. As such, the exemplary embodiments described herein are for illustrative purposes and are not meant to be limiting

What is claimed is:

1. A system for providing prescriptive feedback based on motion of a human subject or object comprising:
   A) a hardware engine operational to gather data about the motion of a subject or object,
   B) a physics engine operatively coupled to the hardware engine and operational to define a model of the subject having a plurality of segments and to process the gathered motion data and correlate the processed motion data with previously stored biomechanical data representing idealized motion models, and
   C) an interactive interface operatively coupled to the data gathering devices and the physics engine and operational to provide prescriptive feedback on flaws identified in the subject's or object's motion,
   wherein the physics engine is further configured to compute an inverse dynamics model of motion of the subject using angular velocity components of each segment, angular acceleration components of each segment, and linear acceleration components of each segment center of mass.

2. The system of claim 1 wherein the interactive interface is further configured for enabling compliance monitoring of the subject's or object's motion.

3. The system of claim 1 wherein the hardware engine comprises a plurality of data gathering devices configured for gathering data about the motion of a subject or object.

4. The system of claim 3 wherein at least one of the plurality of data gathering devices comprises an optical motion capture device to collect three-dimensional positional data from reflective markers placed on the subject or object.

5. The system of claim 3 wherein at least one of the plurality of data gathering devices comprises an inertial measurement unit disposed on the subject or object to collect three-dimensional translation and rotation motion data.

6. The system of claim 3 wherein at least one of the plurality of data gathering devices comprises an infrared scanning device configured to capture three-dimensional point clouds of movement data.

7. The system of claim 3 wherein the physics engine is configured to perform one or more algorithmic processes of the gathered motion data to compute kinematics and kinetics of the subject or object.

8. The system of claim 7 wherein the physics engine is configured to determine points of interest during a particular motion using event detection algorithms.

9. A method for providing prescriptive feedback based on motion of a human subject or object comprising:
   A) gathering data about the motion of a subject or object having at least one segment,
   B) processing the gathered motion data by computing an inverse dynamics model of motion of the subject using angular velocity components of each segment, angular acceleration components of each segment, and linear acceleration components of each segment center of mass and correlating the processed motion data with previously stored biomechanical data representing idealized motion models, and identifying differences therebetween, and
   C) providing prescriptive feedback on flaws identified in the subject's or object's motion.

10. The method of claim 9 further comprising:
   D) enabling compliance monitoring of motion of the subject or object.

11. The method of claim 9 wherein the interactive interface is further configured for enabling compliance monitoring of the subject's or object's motion.

12. The method of claim 9 wherein A) gathering data about the motion of a subject or object comprises:
   A1) gathering data about the motion of a subject or object with an optical motion capture device to collect three-dimensional positional data from reflective markers placed on the subject or object.

13. The method of claim 9 wherein A) gathering data about the motion of a subject or object comprises:
   A1) gathering data about the motion of a subject or object with an inertial measurement unit disposed on the subject or object to collect three-dimensional translation and rotation motion data.

14. The method of claim 9 wherein A) gathering data about the motion of a subject or object comprises:
   A1) gathering data about the motion of a subject or object with an infrared scanning device configured to capture three-dimensional point clouds of movement data.

15. The method of claim 9 wherein B) comprises:
   B1) performing one or more algorithmic processes of the gathered motion data to compute kinematics and kinetics of the subject or object.

16. The method of claim 15 wherein B) comprises:
   B1) determining points of interest during a particular motion using event detection algorithms.

17. A method for providing prescriptive feedback based on motion of a human subject or object comprising:
   A) gathering data about the motion of a subject or object having at least one segment,
   B) processing the motion data by computing any of an inverse dynamics model of motion of the subject using angular velocity components of each segment, angular acceleration components of each segment, and linear acceleration components of a segment center of mass,
   C) correlating the process motion data with previously stored biomechanical data representing idealized motion models, and
   D) providing prescriptive feedback on flaws identified in the motion of the subject or object.

* * * * *